(12) United States Patent
Rah et al.

(10) Patent No.: US 8,426,195 B2
(45) Date of Patent: Apr. 23, 2013

(54) PROMOTER NUCLEIC ACID MOLECULE DERIVED FROM CORYNEBACTERIUM GLUTAMICUM, RECOMBINANT VECTOR COMPRISING THE PROMOTER, HOST CELL COMPRISING THE RECOMBINANT VECTOR AND METHOD OF EXPRESSING GENE USING THE HOST CELL

(75) Inventors: So-Yeon Rah, Seoul (KR); Jae-Woo Jang, Suwon (KR); Sun-Young Lee, Daejeon (KR); Young-Hoon Park, Seongnam (KR); Sang-Jo Lim, Incheon (KR)

(73) Assignee: CJ Cheiljedang Corp. (KR)

( * ) Notice: Subject to any disclaimer, the term of this patent is extended or adjusted under 35 U.S.C. 154(b) by 661 days.

(21) Appl. No.: 12/523,272

(22) PCT Filed: Jan. 15, 2008

(86) PCT No.: PCT/KR2008/000246
§ 371 (c)(1), (2), (4) Date: Jul. 15, 2009

(87) PCT Pub. No.: WO2008/088158
PCT Pub. Date: Jul. 24, 2008

(65) Prior Publication Data
US 2010/0261256 A1 Oct. 14, 2010

(30) Foreign Application Priority Data
Jan. 15, 2007 (KR) .................. 10-2007-0004386

(51) Int. Cl.
C12N 15/00 (2006.01)
C12N 1/20 (2006.01)
C07H 21/04 (2006.01)

(52) U.S. Cl.
USPC ................. 435/320.1; 435/252.32; 536/24.1

(58) Field of Classification Search .................. None
See application file for complete search history.

(56) References Cited

U.S. PATENT DOCUMENTS

| 7,332,310 B2 * | 2/2008 | Nakagawa et al. | 435/115 |
| 2002/0197605 A1 * | 12/2002 | Nakagawa et al. | 435/6 |

FOREIGN PATENT DOCUMENTS

| EP | 1 108 790 A2 * | 6/2001 |
| EP | 1108790 A2 | 6/2001 |
| JP | 2003265177 | 9/2003 |
| JP | 2006288318 | 10/2006 |
| KR | 10-2006-0068505 | 6/2006 |
| KR | 1020060068505 A | 6/2006 |
| KR | 10-2008-0025355 | 3/2008 |
| WO | 2005021765 | 3/2005 |

OTHER PUBLICATIONS

Kalinowski et al., Journal of Biotechnology, 2003; 104: 5-25.*
Miroslav Patek et al., Promoters from Corynebacterium glutamicum: cloning, molecular anaylysis and search for a consensus motif, Microbiology (1996), vol. 142, pp. 1297-1309.
M. Ikeda et al., The Corynebacterium glutamicum genome: features and impacts on biotechnological processes, Appl. Microbiol Biotechnol (2003), vol. 62, pp. 99-109.
M. E. van der Rest et al., A heat shock following electroporation induces highly efficient transformation of Corynebacterium glutamicum with xenogeneic plasmid DNA, Appl. Microbiol Biotechnol (1999), vol. 52, pp. 541-545.
J. Ohnishi et al., A novel methodology employing Corynebacterium glutamicum genome information to generate a new L-lysine-producing mutant, Appl. Microbiol Biotechnol (2002), vol. 58, pp. 217-223.
Pavia Vasicova et al., Analysis of the Corynebacterium glutamicum dapA Promoter, Journal of Bacteriology, Oct. 1999, vol. 181, No. 19, pp. 6188-6191.
Bernhard J. Eikmanns et al., A family of Corynebacterium glutamicum/ Escherichia coli shuttle vectors for cloning, controlled gene expression, and promoter probing, Gene., (1991), vol. 102, pp. 93-98.
Office Action dated Feb. 5, 2010 of the German Patent Application No. 112008000181.2 which corresponds to the PCT application No. PCT/KR2008/000246, Claims translated 4 pages total.
"The complete Corynebacterium glutamicum ATCC 13032 genome sequence and its impact on the production of L-aspartate-derived amino acids and vitamins"; Jorn Kalinowski, Brigitte Bathe, Daniela Bartels, Nicole Bischoff, Michael Bott, Andreas Burkovski, Nicole Dusch, Lothar Eggeling, Bernhard J. Eikmanns, Lars Gaigalat, Alexander Goesmann, Michael Hartmann, Klaus Huthmacher, Reinhard Kramer, Burkhard Linke, Alice C. McHardy, Folker Meyer, Bettina Mockel, Walter Pfefferle, Alfred Puhler, Daniel A. Rey, Christian Ruckert, Oliver Rupp, Hermann Sahm, Volker F. Wendisch, IRIS Wiegrabe, Andreas Tauch; Journal of Biotechnology 104 (2003) 5-25.
Lee, J.K. et al., Nucleotide sequence of the gene encoding the Corynebacterium glutamicum mannose enzyme II and analyses of the deduced protein sequence, FEMS Microbiol Lett., 1994 ;119(1-2):137-145.

\* cited by examiner

Primary Examiner — Vanessa L. Ford
Assistant Examiner — Lakia Tongue
(74) Attorney, Agent, or Firm — Cantor Colburn LLP

(57) ABSTRACT

Provided are a novel promoter nucleic acid molecule having a nucleotide sequence of SEQ ID NO: 1 or 2 derived from *Corynebacterium glutamicum*, a recombinant vector comprising the promoter, a host cell transformed with the vector and a method of expressing genes of interest using the host cell.

14 Claims, 1 Drawing Sheet

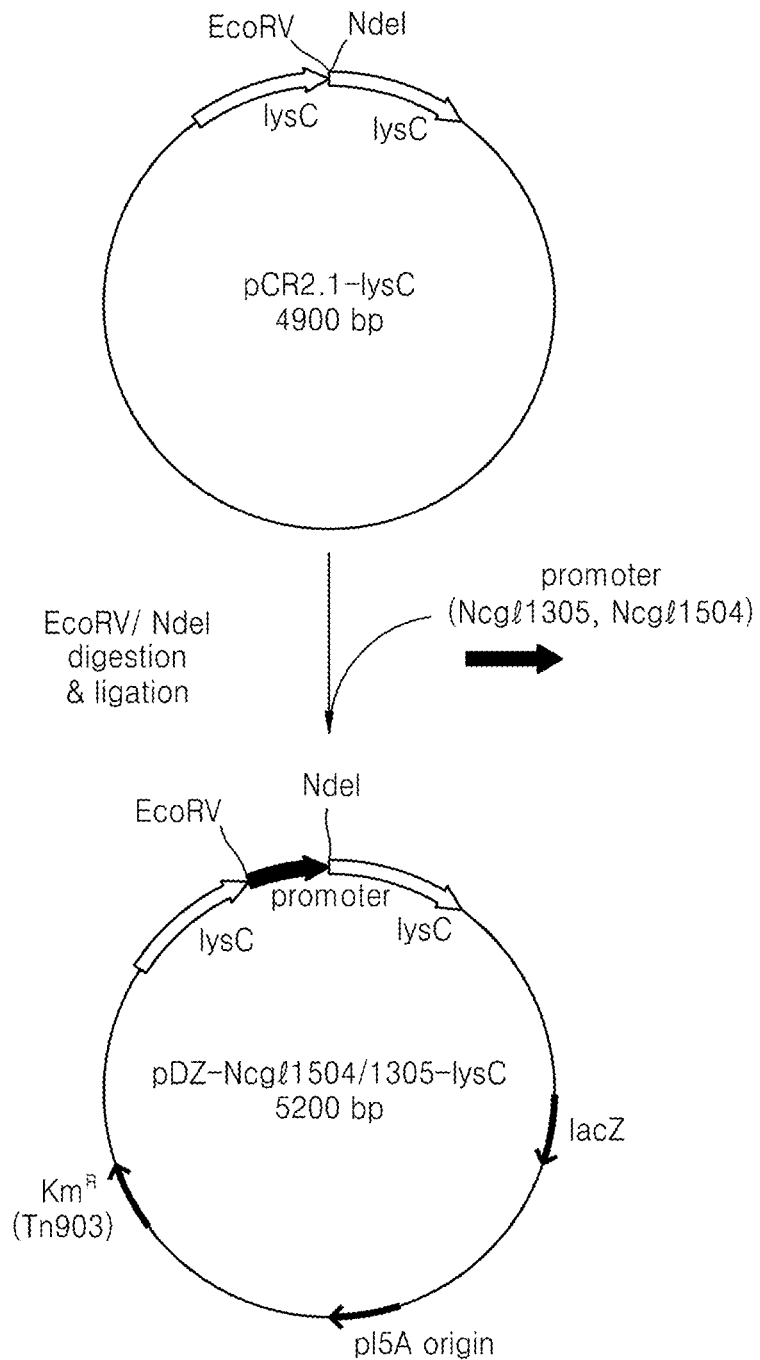

PROMOTER NUCLEIC ACID MOLECULE DERIVED FROM CORYNEBACTERIUM GLUTAMICUM, RECOMBINANT VECTOR COMPRISING THE PROMOTER, HOST CELL COMPRISING THE RECOMBINANT VECTOR AND METHOD OF EXPRESSING GENE USING THE HOST CELL

TECHNICAL FIELD

The present invention relates to a novel promoter nucleic acid molecule derived from *Corynebacterium glutamicum*, a recombinant vector comprising the promoter, a host cell transformed with the recombinant vector and a method of expressing a target gene using the host cell.

BACKGROUND ART

Coryneform bacteria have been widely used to produce chemical substances which have various applications in industries of animal feed, pharmaceuticals, food, and the like including L-lysine, L-threonine and various nucleic acids. In order to develop high yield strains from such coryneform bacteria using genetic engineering and metabolic engineering techniques, expression of genes involved in various metabolic pathways in coryneform bacteria need to be selectively regulated, and thus promoters useful for these gene regulations are required.

Conventional methods of isolating promoters include: (1) a method of using promoter probe vector randomly cloning genomic DNA fragments upstream of a reporter gene expressed only when a cloned fragment contains promoter activity; (2) a method of isolating genes and their promoters from a gene library using gene-specific probe-based hybridization; and (3) a differential hybridization of a gene bank using an inducible cDNA probe and a non-inducible cDNA probe.

In the expression of genes in coryneform bacteria, genes are generally expressed under their control of original promoters (Vasicova, P., et al., J. Bacteriol., 181, 6188-6191, (1999), etc.). However, typical structures of promoter sequences for gene expressions in coryneform bacteria have been unknown unlike other industrial microorganisms such as *Escherichia coli, Bacillus subtilis*, and the like. Thus, promoters for use in coryneform bacteria have been developed by eliminating a promoter region from a gene associated with resistance to antibiotics such as chloramphenicol, introducing into the promoter site a chromosomal DNA fragment isolated from coryneform bacteria with suitable restriction digestion, transforming coryneform bacteria with the resulting DNA molecules, and assessing antibiotic resistance of obtained strains (Eikmanns, B. J., et al., Gene, 102, 93-98, (1991); Patek, M., et al., Microbiology, 142, 1297-1309, (1996)). However, conventionally developed promoter sequences still need to be improved with respect to selectivity of gene expression, expression efficiency of genes, etc.

We developed a novel promoter nucleic acid molecule derived from *Corynebacterium glutamicum* by searching and amplifying putative promoter regions by polymerase chain reaction (PCR), introducing the putative promoter into the initiation site of lysC gene lacking a promoter, and identifying variations in lysC activity via lysine production to select efficient promoters.

DISCLOSURE OF THE INVENTION

The present invention provides a novel promoter nucleic acid molecule derived from *Corynebacterium glutamicum*.

The present invention also provides a recombinant vector comprising a novel promoter nucleic acid molecule derived from *Corynebacterium glutamicum*.

The present invention also provides a host cell transformed with a recombinant vector comprising a novel promoter nucleic acid molecule derived from *Corynebacterium glutamicum*.

The present invention also provides a method of expressing a target gene using a host cell transformed with a recombinant vector comprising a novel promoter nucleic acid molecule derived from *Corynebacterium glutamicum*.

BRIEF DESCRIPTION OF THE DRAWINGS

The above and other objects, features and other advantages of the present invention will be more clearly understood from the following detailed description taken in conjunction with the accompanying drawings, in which:

FIG. 1 schematically shows a process of preparing vectors for exploring promoter activity according to an embodiment of the present invention.

BEST MODE FOR CARRYING OUT THE INVENTION

According to an aspect of the present invention, there is provided a promoter nucleic acid molecule having a nucleotide sequence of SEQ ID NO: 1 or 2.

The nucleotide sequence of the promoter nucleic acid molecule according to the present invention may be modified to a certain degree by one of several recently developed techniques such as directed evolution or site-directed mutagenesis. Those skilled in the art would readily understand that a nucleotide sequence having 70% or higher homology to the sequence of the promoter of the present invention is an equivalent to the promoter of the present invention, as long as it retains promoter activity for expressing a target gene.

Thus, the promoter nucleic acid molecule according to the present invention may include nucleotide sequences which have 70% or higher homology to a nucleotide sequence of SEQ ID NO: 1 or 2 and can be used as a promoter.

The term "homology" used herein indicates a degree of sequence identity to the wild type nucleic acid sequence. The promoter of the present invention may include promoters having a DNA sequence 75% or higher, preferably 85% or higher, more preferably 90% or higher and most preferably 95% or higher identical to the nucleotide sequence of the novel promoter of the present invention. The homology may be compared by the naked eyes or using a commercially available software. According to the commercially available software program, the homology between two or more sequences can be calculated as a percentage (%), and the homology (%) between adjacent sequences may be calculated.

In addition, the promoter nucleic acid molecule of the present invention may include promoter nucleic acid molecules derived from *Corynebacterium glutamicum*, selected from the group consisting of promoters comprising nucleotide sequences complementary to the nucleotide sequences described above.

The term "complementary" used herein indicates that hybridization or base paring is possible between nucleotides or nucleic acids, for example, between the two strands of a double-stranded DNA molecule or between an oligonucleotide primer and a primer binding site of a single-stranded nucleic acid template to be sequenced or amplified.

In addition, the promoter nucleic acid molecule derived from *Corynebacterium glutamicum* of the present invention includes a functional equivalent to the promoter nucleic acid molecule derived from *Corynebacterium glutamicum*. The functional equivalent to the promoter of the present invention which includes functional fragment thereof may include variants having at least one base substitutions, deletions, insertions or combinations thereof.

The *Corynebacterium glutamicum* promoter nucleic acid molecule of the present invention is a promoter derived from coryneform bacterium, and preferably efficiently used as a promoter for expressions of genes of interest in prokaryotic cells, particularly, *Escherichia coli* and coryneform bacteria.

The term "promoter" used herein indicates a DNA region to which a RNA polymerase binds to initiate gene transcription, located upstream of mRNA transcription initiation site, to the 5' direction.

The promoter of the present invention having a nucleotide sequence of SEQ ID NO: 1 or 2 of the present invention may be promoters for gene NCgl1504 (SEQ ID NO: 11) and gene NCgl1305 (SEQ ID NO: 12) selected by analyzing the amount of gene expressions of about 3000 genes of the *Corynebacterium glutamicum* ATCC 13032.

Herein, the 'gene having a nucleotide sequence NCgl1504' and 'gene having a nucleotide sequence NCgl1305' refer to not only genes having nucleotide sequences of SEQ ID NOS: 11 and 12, respectively, derived from *Corynebacterium glutamicum* ATCC 13032 strains, but also genes expressing products substantially identical to those expressed by the NCgl1504 or NCgl1305 in microorganisms belonging to genus *Corynebacterium*. The terms, 'NCgl1504 gene' and 'NCgl1305 gene', respectively refer to 'gene having a nucleotide sequence NCgl1504' and 'gene having a nucleotide sequence NCgl1305'. The term 'substantially identical' used herein indicates activities and regulation mechanisms. The gene having nucleotide sequence NCgl1504 may be a gene having nucleotide sequence of SEQ ID NO: 11 and the gene having nucleotide sequence NCgl1305 may be a gene having nucleotide sequence of SEQ ID NO: 12.

The promoter nucleic acid molecule according to the present invention may be isolated or prepared using a standard molecular biology technique, for example by PCR using appropriate primer sequences. It may also be prepared by a standard synthesis technique using an automated DNA synthesizer.

The present invention also provides a recombinant vector comprising a promoter having a nucleotide sequence of SEQ ID NO: 1 or 2 and a coding sequence of a target gene which is operationally linked to the promoter.

The term "vector" used herein indicates a DNA construct comprising a DNA sequence which is operationally linked to a suitable control sequence for expression in a suitable host cells. The suitable control sequence includes a promoter to direct transcription, an arbitrary operator sequence to regulate such transcription, a sequence encoding a suitable mRNA ribosome binding site and a sequence for transcription and translation. The vector may be a plasmid, a phage particle or simply a potential genome insert. When a vector transforms a compatible host, the vector may replicate and function independently from the host genome, or may be integrated into the genome of the host in some cases. The term "operationally linked" used herein indicates that a gene to be expressed is functionally linked to its control sequences so that the gene is properly expressed.

A recombinant vector comprising a *Corynebacterium glutamicum* promoter nucleic acid molecule according to the present invention may be operationally linked to genes encoding various proteins to recombinationally produce target proteins. The target genes to be expressed using the vector of the present invention may be lysC encoding aspartate kinase, dapB encoding dihydrodipicolinate reductase, or the like, but are not limited thereto.

The target genes according to the present invention may be lysC encoding aspartate kinase. The lysC gene encoding aspartate kinase may have a base sequence of SEQ ID NO: 13 (Ikeda et al, Appl Microbiol Biotechnol. 2002 February; 58(2):217-23 A novel methodology employing *Corynebacterium glutamicum* genome information to generate a new L-lysine-producing mutant).

The recombinant vector according to the present invention may be pDZ-NCgl1504-lysC comprising a promoter having a nucleotide sequence of SEQ ID NO: 1 operationally linked to lysC coding sequence (SEQ ID NO: 13) which is the target gene. The recombinant vector may also be pDZ-NCgl1305-lysC comprising a promoter having a nucleotide sequence of SEQ ID NO: 2 operationally linked to lysC coding sequence (SEQ ID NO: 13) which is the target gene.

The present invention also provides a host cell transformed with a recombinant vector comprising a promoter having a nucleotide sequence of SEQ ID NO: 1 or 2.

The host cell, for example, prokaryotic cells, preferably *Escherichia coli* and coryneform bacteria, and more preferably coryneform bacteria may be transformed with the recombinant vector prepared such that the *Corynebacterium glutamicum* promoter nucleic acid molecule is operationally linked to the gene encoding a target protein in order to express the target protein.

The "coryneform bacteria" may be bacteria belonging to genus *Corynebacterium* or genus *Brevibacterium*, particularly *Corynebacterium glutamicum*, and more particularly *Corynebacterium glutamicum* ATCC 13032. The coryneform bacteria of the present invention may include other strains of the genus *Corynebacterium, Corynebacterium thermoaminogenes* FERM BP-1539, *Brevibacterium flavum* ATCC 14067, *Brevibacterium lactofermentum* ATCC 13869 and a mutant thereof producing L-amino acid, or *Corynebacterium glutamicum* KFCC 10881, *Corynebacterium glutamicum* KFCC 11001, and the like.

The term "transformation" used herein indicates the introduction of DNA into a host in such a way that it can be replicated either as an extrachromosomal element or by chromosomal integration.

The host cell may be a *Corynebacterium* transformed with a recombinant vector comprising a promoter having a nucleotide sequence of SEQ ID NO: 1 and lysC (SEQ ID NO: 13) operationally linked to the promoter. The host cell may preferably be *Corynebacterium glutamicum* (Deposition No. KCCM 10831P, deposited Dec. 28, 2006 under the Budapest Treaty in the International Depository Authority, Korean Culture Center of Microorganisms (KCCM), 361-221, Yurim B/D, Hongje-1-dong, Seodaemun-gu, Seoul 120-091, Republic of Korea, on Dec. 28, 2006).

The host cell may also be a *Corynebacterium* transformed with a recombinant vector comprising a promoter having a nucleotide sequence of SEQ ID NO: 2 and lysC (SEQ ID NO: 13) operationally linked to the promoter. The host cell may preferably be *Corynebacterium glutamicum* (Deposition No. KCCM 10830P, deposited Dec. 28, 2006 under the Budapest Treaty in the International Depository Authority, Korean Culture Center of Microorganisms (KCCM), 361-221, Yurim B/D, Hongje-1-dong, Seodaemun-gu, Seoul 120-091, Republic of Korea, on Dec. 28, 2006).

The present invention also provides a method of expressing a target gene, comprising culturing a host cell transformed with a recombinant vector having a promoter nucleic acid molecule derived from *Corynebacterium glutamicum*.

The target gene which is operationally linked to the promoter having a nucleotide sequence of SEQ ID NO: 1 or 2 may be genes encoding proteins associated with synthesis of the final products such as lysine and threonine. The term "expressing a target gene" used herein indicates producing the final product of a synthetic pathway I which the protein encoded by the target gene is involved. Thus, the method of expressing a target gene may be a method of producing the final product of a synthetic pathway in which a protein encoded by the target gene is involved, by culturing a host cell transformed with a recombinant vector including the target gene.

The final product may be lysine. That is, the present invention may provide a method of producing lysine, comprising culturing a host cell transformed with a recombinant vector comprising lysC encoding a protein involved in lysine synthesis and a promoter having a nucleotide sequence of SEQ ID NO: 1 or 2 operationally linked to the gene.

In the synthesis method of lysine according to the present invention, the host cell may be *Corynebacterium glutanicum* KCCM 10831P or Coryneform bacterium KCCM 10830P transformed with a recombinant vector including the promoter having a nucleotide sequence of SEQ ID NO:1 or 2 which is operationally linked to the target gene, lysC of SEQ ID NO:13.

The cultivation of the transformed host cells (transformants) may be performed according to commonly used methods in the art. The known cultivation methods are disclosed by Chmiel, (Bioprozesstechnik 1. Einfuhrung in die Bioverfahrenstechnik (Gustav Fischer Verlag, Stuttgart, 1991); and Storhas (Bioreaktoren and periphere Einrichtungen (Vieweg Verlag, Braunschweig/Wiesbaden, 1994)).

Culture media used for the cultivation need to meet requirements for growth of particular strains in an appropriate manner. Culture media for *Corynebacterium* strains are disclosed in, for example, Manual of Methods for General Bacteriology. American Society for Bacteriology. Washington D.C., USA, 1981. A carbon source for the culture media may be carbohydrate such as glucose, saccharose, lactose, fructose, maltose, starch and cellulose, oil and fat such as soybean oil, sunflower oil, caster oil and coconut oil, a fatty acid such as palmitic acid, stearic acid and linolenic acid, an alcohol such as glycerol and ethanol, and an organic acid such as acetic acid. The carbon source may be used alone or in a mixture. A nitrogen source may also be peptone, yeast extract, meat extract, malt extract, corn steep liquor, soy meal and urea or an inorganic compound, for example, ammonium sulfate, ammonium chloride, ammonium phosphate, ammonium carbonate and ammonium nitrate. The nitrogen source may be used alone or in a mixture. A phosphorous source may be potassium dihydrogen phosphate, dipotassium hydrogen phosphate or a sodium salt thereof. In addition, the culture media should contain a metal salt such as magnesium sulfate or iron sulfate, essential for the growth. Finally, the culture medium may further include essential substances for growth such as amino acids and vitamins. In addition, suitable precursors may also be added to the culture media. Those components of culture media may be added to the culture media on a batch or continuous basis during the cultivation.

The pH of the culture media can be regulated using a basic compound such as sodium hydroxide, potassium hydroxide and ammonia or an acidic compound such as phosphoric acid or sulfuric acid in an appropriate manner. In addition, foam formation may be prevented using an anti-foaming agent such as fatty acid polyglycol ester. Oxygen or an oxygen-containing gas, for example air, may be introduced into culture media in order to maintain an aerated state. The temperature of culture media may be in the range of 20 to 45° C., and preferably 25 to 40° C. The cultivation is continued until the amount of produced target substance reaches its maximum. In general, the cultivation is performed for 10 to 160 hours.

The present invention will be described in greater detail with reference to the following examples. The following examples are for illustrative purposes only and are not intended to limit the scope of the invention.

Example 1

Preparation of Recombinant Vector Comprising Novel Promoter Sequences

1. Selection of Candidate Genes for Novel Promoter Derived from *Corynebacterium glutamicum*

*Corynebacterium glutamicum* ATCC 13032 was cultured in a 5 L fermenter, and cells were collected. The mRNA expression levels of about 3000 genes of *Corynebacterium glutamicum* ATCC 13032 was determined using genome DNA chips (cDNA chips, Genomictree, Inc., Korea). NCgl1504 and NCgl1305 genes which account for 0.88% and 0.43% based on the total genome expression, respectively, were selected as candidate genes for a novel promoter of the present invention.

2. Amplification of DNA Fragments of Putative Promoter Regions

The nucleotide sequences of genome of *Corynebacterium glutamicum* have been already fully determined and are well known (Appl. Microbiol. Biotechnol., 62(2-3), 99-109 (2003): GenBank Accession No. NC_003450). Sequence information of proteins (NCgl1504 and NCgl1305) was obtained from the National Institutes of Health (NIH) GenBank (U.S.A.) database. In order to amplify putative promoter regions (SEQ ID NO: 1—promoter region of NCgl1504, SEQ ID NO: 2—promoter region of NCgl1305) located upstream of open reading frame (ORF) of each gene, primers 1-4 including EcoRV/BamHI and NdeI restriction sites were synthesized based on the reported nucleotide sequences. Putative promoter regions of NCgl1504 and NCgl1305 genes were amplified in PCR using chromosomal DNA of *Corynebacterium glutamicum* ATCC 13032 as a template, respectively with primers 1 and 2 (SEQ ID NOS: 3 and 4) and primers 3 and 4 (SEQ ID NOS: 5 and 6) [Sambrook et al, Molecular Cloning, a Laboratory Manual (1989), Cold Spring Harbor Laboratories] with 30 cycles of denaturation at 94° C., annealing at 55° C. for 1 min and polymerization at 72° C. for 30 sec.

3. Preparation of Recombinant Vector for Chromosomal Integration for Determining Promoter Activity In order to determine activity of putative promoter regions of the obtained NCgl1504 and NCgl1305 in *Corynebacterium* chromosomes, we used vector pDZ for chromosomal integration (Korean Patent Application No. 1-2006-089672) developed by Cheiljedang Corporation using pACYC177 (New England Biolab, GenBank accetion #X06402), a cloning vector for *E. coli* as a basic vector. In order to insert genes into *Corynebacterium* chromosome, a novel promoter having a nucleotide sequence of SEQ ID NOS: 1 or 2 was inserted before the initiation site of lysC to obtain pDZ-Ncgl1504-lysC or pDZ-Ncgl1305-lysC vectors, respectively.

A recombinant vector in which putative promoter sites of NCgl1504 and NCgl1305 were inserted into lysC gene was prepared in the following manner. In order to amplify lysC of SEQ ID NO: 13, chromosomal DNA of *Corynebacterium glutamicum* ATCC 13032 was used as a template and PCR was performed using primers 5 and 6 (SEQ ID NOS: 7 and 8) and primers 7 and 8 (SEQ ID NOS: 9 and 10) (PCR conditions: 30 cycles of denaturation at 94° C., annealing at 55° C. for 1 min and elongation at 72° C. for 30 sec. LysC fragments amplified using TOPO Cloning Kit (Invitrogen) were digested with EcoRV and Klenau, the two blunt-ended fragments were ligated and cloned into pCR2.1-lysC. Then, promoter sites of pCR.2.1-lysC and NCgl1504 or NCgl1305 were cleaved using EcoRV and NdeI, and novel promoters of SEQ ID NO: 1 or 2 was inserted on the restriction sites using a DNA ligase. Then, the cloned fragments were transferred to the pDZ vector to prepare pDZ-Ncgl1504-lysC and pDZ-Ncgl1305-lysC vectors as shown in FIG. 1.

Example 2

Transformation with Recombinant Strains Including Novel Promoter Sequences

*Corynebacterium glutamicum* KFCC 10881, a L-lysine-producing strain was transformed using the prepared recombinant vector pDZ-NCgl1504-lysC or pDZ-NCgl1305-lysC by electric pulse as disclosed in Appl. Microbiol. Biotechnol. (1999) 52:541-545. Transformed strains were selected in a selective medium including 25 mg/L of kanamycin (10 g/L of beef extract, 10 g/L of peptone, 5 g/L of yeast extract, 5 g/L of sodium chloride, 3.7 g/L of Brain Heart Infusion (BHI) and 9.1 g/L of sorbitol) in which the novel promoter on the reactor is integrated into the chromosome by homologous recombination. The insertion of the vector was identified whether the strains turned blue in a solid medium including X-gal (5-bromo-4-chloro-3-indolyl-β-D-galactoside). The strains in which the vector is inserted into the chromosome via the first crossover were cultured by shaking in a nutrient culture medium at 30° C. for 8 hours, diluted to $10^4$ to $10^{-10}$ respectively and plated onto a solid medium including X-gal. Most of the colonies showed blue color, and strains in which inserted vector sequences was removed by the second crossover were screened by selecting white colonies. Using susceptibility to kanamycin, selected colonies were identified and finally confirmed by sequencing. The strain in which the promoter of lysC gene was replaced by Ncgl1504 was named as CA01-0037, and strains in which the promoter of lysC gene was replaced by Ncgl1305 were referred to as CA01-0036, and they were respectively deposited as KCCM 10831P and KCCM 10830P with the Korean Culture Center of Microorganisms on Dec. 28, 2006.

Example 3

Activity of Promoter Sequence in *Corynebacterium*

The transformed strains were cultured to analyze the activity of promoter sequences as follows.

Each transformed *Corynebacterium glutamicum* strain was inoculated at a ratio of 1:20 in a 250 ml corner-baffle flask containing 25 ml of a culture medium [20 g of glucose, 5 g of ammonium sulfate, 5 g of yeast extract, 1.5 g of urea, 4 g of $KH_2PO_4$, 8 g of $K_2HPO_4$, 0.5 g of $MgSO_4 \cdot 7H_2O$, 150 µg of biotin, 1.5 mg of thiamine hydrochloride, 3 mg of calcium pantothenate, 3 mg of nicotinamide (based on 1 L of distilled water), pH 7.2] and was cultured at 30° C. while shaking at 200 rpm until the culture reached the mid-exponential growth phase ($OD_{600}$=10). When the cultivation is terminated, the cells were collected by centrifugation, were suspended in 100 mM Tris-HCl buffer (pH 7.0), were lysed by sonication, and then were high-speed-centrifuged to obtain a supernatant. 1 mg of proteins from the supernatant was used to measure the activity of lysC enzyme (Black & Wright (1955b)). As a result, the change in activity of lysC was confirmed in strains in which the promoter for lysC was replaced by NCgl1504 or NCgl1305 as shown in the following Table.

TABLE

Comparison of promoter activity by lysine addition

| Strain | Relative degree of promoter expression |
|---|---|
| KFCC 10881 | 1 |
| CA01-0036(KCCM 10830) | 0.74 |
| CA01-0037(KCCM 10831) | 1.67 |

INDUSTRIAL APPLICABILITY

According to the present invention, a novel promoter nucleic acid sequence derived from *Corynebacterium glutamicum* is provided for use in efficient expression of a gene of interest.

The invention claimed is:

1. A promoter nucleic acid molecule consisting of a nucleotide sequence of SEQ ID NO: 1 or 2.

2. A recombinant vector comprising the promoter of claim 1 which is operationally linked to a coding sequence of a target gene.

3. A host cell transformed with the recombinant vector of claim 2.

4. The host cell of claim 3, which belongs to genus *Corynebacterium*.

5. The host cell of claim 4, which is *Corynebacterium glutamicum* KCCM (Korean Culture Center of Microorganisms) 10831P, transformed with a recombinant vector comprising a promoter designated as SEQ ID NO: 1 operationally linked to a coding sequence of lysC gene.

6. The host cell of claim 4, which is *Corynebacterium glutamicum* KCCM (Korean Culture Center of Microorganisms) 10830P, transformed with a recombinant vector comprising a promoter designated as SEQ ID NO: 2 operationally linked to a coding sequence of lysC gene.

7. A method of expressing a target gene, the method comprising culturing a host cell according to claim 3.

8. The method of claim 7, wherein the target gene is lysC gene.

9. A method of expressing a target gene, the method comprising culturing a host cell according to claim 4.

10. A method of expressing a target gene, the method comprising culturing a host cell according to claim 5.

11. A method of expressing a target gene, the method comprising culturing a host cell according to claim 6.

12. The method of claim 9, wherein the target gene is lysC gene.

13. The method of claim 10, wherein the target gene is lysC gene.

14. The method of claim 11, wherein the target gene is lysC gene.

* * * * *

SEQUENCE LISTING

```
<160> NUMBER OF SEQ ID NOS: 13

<210> SEQ ID NO 1
<211> LENGTH: 500
<212> TYPE: DNA
<213> ORGANISM: Corynebacterium glutamicum
<220> FEATURE:
<221> NAME/KEY: promoter
<222> LOCATION: (1)..(500)
<223> OTHER INFORMATION: NCgl1504 promoter

<400> SEQUENCE: 1
agcgttgccc ctaaagggct ctgctcgtct tccacgtgga gggtcgctga tctggaacca      60
gcggtgccga tgcgcggcaa agtgtcgaga aattggcgta ggggacgagg tgcccgagga     120
```

```
aaccattttc tgttttcagg ggcgttcgaa ttgggttgaa tctgctcgtc cttcgtcact    180
cgcatcattc tacgcaaggg agcggagaac atttacctcg catcagagtc tggtggtgac    240 ccgaagggg  atagtgtgag ctaaatctca aattatattc attttcggta attggaatga    300
agttttaaaa cacaccacct gtggccagca taaataaggt tacctttggt tggcttaggg    360
ttcgcttagt ttttatttat tgatgatttt tctacgtcta tttgcgctgg taggggggaa    420
gggattggac acgggaatgg aattaggaa  cacttgtgtt gtctaaaggt gaaagctaaa    480
tcaagcagga ggtgacacca                                                500
```

```
<210> SEQ ID NO 2
<211> LENGTH: 500
<212> TYPE: DNA
<213> ORGANISM: Corynebacterium glutamicum
<220> FEATURE:
<221> NAME/KEY: promoter
<222> LOCATION: (1)..(500)
<223> OTHER INFORMATION: Promoter for NCgl1305

<400> SEQUENCE: 2
```

```
ttttggcggg cgcttcggcg aaaatacatg ggcctacaac gccgtctaag cgtgaaactg     60
ggggatgggg atacctggaa tcattcgggg acgtgatgcg gtggaggggt ggtgcgggca    120
taatctgaca gtgtgtccgt tttcattttc aaaaaatgca ggtcggacat attcaaaagt    180 attaccttt  tggtttgtct gtattcagct tgttttgggt gggtttccgg cttatcatga    240
tgggtgactt accgcttaat tggaaaaaag tgtgatccac cacaaatcta ttgcggggga    300
gcctgggaaa ctaggtaaaa attttgcca aattgtgcaa tcgttttcac aacctgagaa    360
tgtcacaaca cattaagtgg taggcgctga ggaatcgaat ccgattcttt ttcggcccaa    420
ttcgtaacgg cgatcctctt aagtggacaa gaaagtctct tgcccgcggg agacagaccc    480
tacgtttaga aaggtttgac                                                500
```

```
<210> SEQ ID NO 3
<211> LENGTH: 33
<212> TYPE: DNA
<213> ORGANISM: Artificial Sequence
<220> FEATURE:
<223> OTHER INFORMATION: Primer 1 for amplifying the promoter of
      NCgl1504 gene

<400> SEQUENCE: 3
```

```
aggatatcgg atccagcgga gacatttacc tcg                                  33
```

```
<210> SEQ ID NO 4
<211> LENGTH: 26
<212> TYPE: DNA
<213> ORGANISM: Artificial Sequence
<220> FEATURE:
<223> OTHER INFORMATION: Primer 2 for amplifying the promoter of
      NCgl1504 gene

<400> SEQUENCE: 4
```

```
gagcatatgt gtcacctcct gcttga                                          26
```

```
<210> SEQ ID NO 5
<211> LENGTH: 33
<212> TYPE: DNA
<213> ORGANISM: Artificial Sequence
<220> FEATURE:
<223> OTHER INFORMATION: Primer 3 for amplifying the promoter of
      NCgl1305 gene

<400> SEQUENCE: 5
```
aggatatcgg atccgtattc agcttgtttt ggg                                    33

<210> SEQ ID NO 6
<211> LENGTH: 26
<212> TYPE: DNA
<213> ORGANISM: Artificial Sequence
<220> FEATURE:
<223> OTHER INFORMATION: Primer 4 for amplifying the promoter of
      NCgl1305 gene

<400> SEQUENCE: 6
gagcatatga aacctttcta aacgta                                            26

<210> SEQ ID NO 7
<211> LENGTH: 20
<212> TYPE: DNA
<213> ORGANISM: Artificial Sequence
<220> FEATURE:
<223> OTHER INFORMATION: Primer 5 for amplifying lysC

<400> SEQUENCE: 7
gacaggacaa gcactggttg                                                   20

<210> SEQ ID NO 8
<211> LENGTH: 27
<212> TYPE: DNA
<213> ORGANISM: Artificial Sequence
<220> FEATURE:
<223> OTHER INFORMATION: Primer 6 for amplifying lysC

<400> SEQUENCE: 8
aggatatcct ttgtgcacct ttcgatc                                           27

<210> SEQ ID NO 9
<211> LENGTH: 28
<212> TYPE: DNA
<213> ORGANISM: Artificial Sequence
<220> FEATURE:
<223> OTHER INFORMATION: Primer 7 for amplifying lysC

<400> SEQUENCE: 9
gatatcatat ggccctggtc gtacagaa                                          28

<210> SEQ ID NO 10
<211> LENGTH: 25
<212> TYPE: DNA
<213> ORGANISM: Artificial Sequence
<220> FEATURE:
<223> OTHER INFORMATION: Primer 8 for amplifying lysC

<400> SEQUENCE: 10
ccagcctgag agcccgtgaa agatt                                             25

<210> SEQ ID NO 11
<211> LENGTH: 687
<212> TYPE: DNA
<213> ORGANISM: Corynebacterium glutamicum
<220> FEATURE:
<221> NAME/KEY: gene
<222> LOCATION: (1)..(687)
<223> OTHER INFORMATION: NCgl1504

<400> SEQUENCE: 11
gtgggagatg ttgtaaaagg caacgacgcg cacaccggag acggtgatac gcgccgaaaa       60
attcttctca tcctgttgga acgtgcaccg gtgatcgctt cagatattgc tgaacagctt      120

```
cagcttttcaa ctgtgggagt gcgcaggcac ctagacaact tggttgaaga aaatctggcg      180
gaggcggcaa atccgcgcca gaacccatat gagcccaaaa tgcgcggtag gccagcaaaa      240
acttatcggc ttactgataa aggtcgctca atcttcggcc acgaatatga ttcccttgct      300
gcggcagctc tagccactct tcgagaggtc ggcggagatg atgcagtaag gcaatttgct      360
agaaagcgga tcgaaacaat tgttgagggt attaccccag cagatgtcac agatcaatca      420
atcgaagata cagccaaatc tttagttgaa gcttttagtc ggcatggtta tgcagcaact      480
gtcgatgcca ctcgaaacgg gttgcaactc tgccagcatc actgtccaat atctacagtc      540
gccacggaat tccggaact gtgtgaggca gagcatcaag cagtctcaga acttttgggg       600
cagcacacgc aaccattggc aacaatcgcg gacggccacg gcatctgcac aacaaatatt      660
ccattgacac ccatcaaaca ctcctga                                          687

<210> SEQ ID NO 12
<211> LENGTH: 2052
<212> TYPE: DNA
<213> ORGANISM: Corynebacterium glutamicum
<220> FEATURE:
<221> NAME/KEY: gene
<222> LOCATION: (1)..(2052)
<223> OTHER INFORMATION: NCgl1305

<400> SEQUENCE: 12
atggcgtcca aactgacgac gacatcgcaa catattctgg aaaaccttgg tggaccagac       60
aatattactt cgatgactca ctgtgcgact cgccttcgct tccaagtgaa ggatcaatcc      120
attgttgatc aacaagaaat tgactccgac ccatcagttc ttggcgtagt accccaagga      180
tccaccggta tgcaggtggt gatgggtgga tctgttgcaa actattacca agaaatcctc      240
aaacttgatg gaatgaagca cttcgccgac ggtgaagcta cagagagttc atccaagaag      300
gaatacggcg gagtccgtgg caagtactcg tggattgact acgccttcga gttcttgtct      360
gatactttcc gaccaatcct gtgggccctg cttggtgcct cactgattat taccttgttg      420
gttcttgcgg atactttcgg tttgcaagac ttccgcgctc caatggatga gcagcctgat      480
acttatgtat tcctgcactc catgtggcgc tcggtcttct acttcctgcc aattatggtt      540
ggtgccaccg cagctcgaaa gctcggcgca aacgagtgga ttggtgcagc tattccagcc      600
gcacttctta ctccagaatt cttggcactg ggttctgccg gcgataccgt cacagtcttt      660
ggcctgccaa tggttctgaa tgactactcc ggacaggtat cccaccgct gattgcagca       720 attggtctgt actgggtgga aaagggactg aagaagatca tccctgaagc agtccaaatg      780
gtgttcgtcc cattcttctc cctgctgatt atgatcccag cgaccgcatt cctgcttgga      840
cctttcggca tcggtgttgg taacggaatt tccaacctgc ttgaagcgat taacaacttc      900
agcccattta ttctttccat cgttatccca ttgctctacc cattcttggt tccacttgga      960
ttgcactggc cactaaacgc catcatgatc cagaacatca cacccctggg ttacgacttc     1020
attcagggac caatgggtgc ctggaacttc gcctgcttcg gcctggtcac cggcgtgttc     1080
ttgctctcca ttaaggaacg aaacaaggcc atgcgtcagg tttccctggg tggcatgttg     1140 gctggttttgc tcggcggcat ttccgagcct tccctctacg tgttctgct ccgattcaag     1200 aagacctact tccgcctcct gccgggttgt ttggcaggcg gtatcgtgat gggcatcttc     1260
gacatcaagg cgtacgcttt cgtgttcacc tccttgctta ccatcccagc aatggaccca     1320
tggttgggct acaccattgg tatcgcagtt gcattcttcg tttccatgtt ccttgttctc     1380
gcactggact accgttccaa cgaagagcgc gatgaggcac gtgcaaaggt tgctgctgac     1440
```

```
aagcaggcag aagaagatct gaaggcagaa gctaatgcaa ctcctgcagc tccagtagct    1500
gctgcaggtg cggagccgg tgcaggtgca ggagccgctg ctggcgctgc aaccgccgtg    1560
gcagctaagc cgaagctggc cgctggggaa gtagtggaca ttgttttcccc actcgaaggc   1620 aaggcaattc cactttctga agtacctgac ccaatctttg cagcaggcaa gcttggacca    1680
ggcattgcaa tccaaccaac tggaaacacc gttgttgctc cagcagacgc tactgtcatc    1740
cttgtccaga atctggaca cgcagtggca ttgcgcttag atagcggagt tgaaatcctt     1800
gtccacgttg gattggacac cgtgcaattg ggcggcgaag gcttcaccgt tcacgttgag    1860
cgcaggcagc aagtcaaggc gggggatcca ctgatcactt ttgacgctga cttcattcga    1920
tccaaggatc tacctttgat caccccagtt gtggtgtcta acgccgcgaa attcggtgaa    1980
attgaaggta ttcctgcaga tcaggcaaat tcttccacga ctgtgatcaa ggtcaacggc    2040
aagaacgagt aa                                                       2052

<210> SEQ ID NO 13
<211> LENGTH: 1500
<212> TYPE: DNA
<213> ORGANISM: Corynebacterium glutamicum
<220> FEATURE:
<221> NAME/KEY: gene
<222> LOCATION: (1)..(1500)
<223> OTHER INFORMATION: 217: start 1490:stop(lysC gene)

<400> SEQUENCE: 13
tcgcgaagta gcacctgtca cttttgtctc aaatattaaa tcgaatatca atatatggtc     60
tgtttattgg aacgcgtccc agtggctgag acgcatccgc taaagcccca ggaaccctgt    120
gcagaaagaa aacactcctc tggctaggta gacacagttt ataaaggtag agttgagcgg    180
gtaactgtca gcacgtagat cgaaaggtgc acaaggtgg ccctggtcgt acagaaatat     240
ggcggttcct cgcttgagag tgcggaacgc attagaaacg tcgctgaacg gatcgttgcc    300
accaagaagg ctggaaatga tgtcgtggtt gtcgtctccg caatgggaga caccacggat    360
gaacttctag aacttgcagc ggcagtgaat cccgttccgc cagctcgtga aatggatatg    420
ctcctgactg ctggtgagcg tatttctaac gctctcgtcg ccatggctat tgagtccctt    480
ggcgcagaag cccaatcttt cacgggctct caggctggtg tgctcaccac cgagcgccac    540
ggaaacgcac gcattgttga tgtcactcca ggtcgtgtgc gtgaagcact cgatgagggc    600
aagatctgca ttgttgctgg tttccagggt gttaataaag aaacccgcga tgtcaccacg    660
ttgggtcgtg gtggttctga caccactgca gttgcgttgg cagctgcttt gaacgctgat    720
gtgtgtgaga tttactcgga cgttgacggt gtgtataccg ctgacccgcg catcgttcct    780
aatgcacaga agctggaaaa gctcagcttc gaagaaatgc tggaacttgc tgctgttggc    840
tccaagattt tggtgctgcg cagtgttgaa tacgctcgtg cattcaatgt gccacttcgc    900
gtacgctcgt cttatagtaa tgatcccggc actttgattg ccggctctat ggaggatatt    960
cctgtggaag aagcagtcct taccggtgtc gcaaccgaca agtccgaagc caaagtaacc    1020
gttctgggta tttccgataa gccaggcgag gctgcgaagg ttttccgtgc gttggctgat    1080
gcagaaatca acattgacat ggttctgcag aacgtctctt ctgtagaaga cggcaccacc    1140
gacatcacct tcacctgccc tcgttccgac ggccgccgcg cgatggagat cttgaagaag    1200
```

-continued

```
cttcaggttc agggcaactg gaccaatgtg ctttacgacg accaggtcgg caaagtctcc    1260
ctcgtgggtg ctggcatgaa gtctcaccca ggtgttaccg cagagttcat ggaagctctg    1320
cgcgatgtca acgtgaacat cgaattgatt tccacctctg agattcgtat ttccgtgctg    1380
atccgtgaag atgatctgga tgctgctgca cgtgcattgc atgagcagtt ccagctgggc    1440
ggcgaagacg aagccgtcgt ttatgcaggc accggacgct aaagttttaa aggagtagtt    1500
```